United States Patent [19]
Lazzara et al.

[11] Patent Number: 5,000,686
[45] Date of Patent: Mar. 19, 1991

[54] DENTAL IMPLANT FIXTURE

[75] Inventors: Richard J. Lazzara, Lake Worth; Keith D. Beaty, West Palm Beach, both of Fla.

[73] Assignee: Implant Innovations, Inc., West Palm Beach, Fla.

[21] Appl. No.: 459,529

[22] Filed: Jan. 2, 1990

[51] Int. Cl.⁵ .................................................. A61C 8/00
[52] U.S. Cl. ....................................................... 433/174
[58] Field of Search ............................ 433/174, 221, 173

[56] References Cited
U.S. PATENT DOCUMENTS 4,626,214  12/1986  Artal .................................. 433/174
4,668,191  5/1987  Plischka ............................ 433/174
4,863,383  9/1989  Grafelmann ..................... 433/174

FOREIGN PATENT DOCUMENTS 2199502  7/1988  United Kingdom ............... 433/174

*Primary Examiner*—Cary E. Stone
*Attorney, Agent, or Firm*—Alfred H. Rosen

[57] ABSTRACT

A dental implant fixture of cylindrical cross-section has a diameter limited to not more than about 3 mm., for use in narrow jawbone ridges. The diameter of the fixture is smaller at its apical end than at its gingival end. Screw threads on the outer surface of the fixture are peak-limited to the locus of a cylinder of uniform diameter that is larger than the diameter of the fixture at its apical end.

8 Claims, 1 Drawing Sheet

DENTAL IMPLANT FIXTURE

BACKGROUND OF THE INVENTION

This invention relates to dental implant fixtures, more particularly to cylindrical fixtures which have a smaller external diameter than has up to now been available, for use in thin sections of human jawbones. This application is additional to our co-pending application Ser. No. 283,977 filed 12/13/88.

Cylindrical-shaped dental implant fixtures are known; they are in two broadly-defined groups—some having screw threads on all or part of the exterior wall, and some without threads. All are fitted into a pre-drilled bore prepared in the patient's jawbone, those with screw threads being screwed in, like a machine screw. Of the latter, some are self-tapping, and in some cases the prepared bore is pre-tapped to receive the threaded implant. In all cases the thickness of the section of the patient's jawbone to be prepared limits the diameter of the prepared bore that can be drilled in it. It is general dental practice to leave at least one mm. thickness of jawbone wall on either side of the prepared bore. Up to now cylindrical dental implant fixtures have been available in diameters ranging from about 4.0 mm. down to about 3.3 mm. This has limited the thickness of human jawbones in which dental implant fixtures can be installed to not less that about 5.3 mm, effectively barring the availability of dental implant fixtures in many situations where periodontic restoration is otherwise indicated.

Placement of cylindrical implants in narrow jawbone ridges often is only possible if bone is removed; i.e.: cutting a way of the narrow ridge until a point of sufficient ridge-width to accept the implant is reached. Availability of a narrower implant will reduce, and in some cases eliminate the need for such a procedure.

Dental implant fixtures are fitted with bores to receive and support transition components which in turn support a prosthodontic restoration. In the case of a cylindrical-shaped fixture this bore is usually coaxial in the fixture; frequently it is internally-threaded. The thickness of the material of the fixture between the outer wall (minor diameter of the external thread) and the wall of the receiving bore at its major diameter cannot be reduced below the minimum strength requirements of the fixture and its related transition components. Up to now these requirements have contributed to restricting the above-mentioned smaller diameter to about 3.3 mm.

GENERAL DESCRIPTION OF THE INVENTION

The principal object of this invention is to provide a generally cylindrical dental implant fixture which has a smaller exterior diameter than has been available previously, so that dental implant fixtures will be able to be installed in thinner sections of human jawbones than has previously been possible. To accomplish this object the invention provides a new, thinner dental implant fixture having a new configuration of implant body and external screw threads, as well as a new combination of the implant fixtures and a prepared bore specially contoured to receive it. The implant body is in the form of a tapered (e.g.: cone-shaped) male shaft having screw threads on its exterior. The threads are of uniform pitch. The roots of of the threads lie on the surface of the tapered shaft, while the peaks of the threads are truncated on the locus of a cylinder that is coaxial with the tapered shaft. The shaft extends between a gingival region of the implant fixture and an apical end, the wider end of the shaft being in the gingival region. The diameter of the wider end of the shaft is preferably smaller than the diameter of the cylinder locus of the truncated thread peaks. Thus, the narrower end of the shaft is at the apical end of the implant fixture, where the threads have maximum peak-to-trough depth. As the threads progress axially away from the apical end, peak-to-trough depth diminishes and the shaft becomes wider. Preferably, the shaft is uniformly wider around the receiving bore, providing a uniformly thick wall of material between the internal bore thread (major diameter) and the external thread root (minor diameter). This uniformly thick wall is in the areas of highest stress on the implant fixture; it allows the fabrication of a 2.8 to 2.9 mm., diameter cylindrical implant fixture which has adequate strength. With this combination of cylindrical-peak-limited threads on a male tapered shaft the threads can engage the bottom side walls of a bore to pull the shaft tightly into the bore, at the same time bringing the shaft into intimate contact with the entire side walls of the prepared bore in the host bone. Preferably the prepared bore is tapered to mate with the taper of the shaft when the latter is fully seated in the bore.

Dental fixtures according to the invention provide, in combination, two recognized means for promoting osseointegration of a dental implant fixture in human jawbone. The threads with increasing purchase at the apical end of the fixture serve to anchor the fixture at the side walls of the prepared bore well inside the jawbone near the bottom of the bore. This anchor effect immobilizes the implant fixture during the healing period, satisfying a well-recognized requirement for successful osseointegration. The side walls of the shaft are brought into intimate proximity with the side walls of the prepared bore where the two can be held relatively fixed together for a sufficient time to allow osseointegration to take place. The wider part of the shaft near the gingival aspect of the jawbone maintains this intimate contact during and after the osseointegration process. Failure to maintain good contact between the implant fixture and the bone tissue near the gingival aspect of the jawbone has in the past led to bone resorption in that region with the use of some prior-art dental implant fixtures. This invention is, accordingly, useful not only to satisfy its principal object but also to improve dental implant fixtures in general.

Dental implant fixtures according to the invention can be made significantly less than 3.00 mm in shaft diameter. In one example a tapered shaft has an apical-end diameter of 2.21 mm, and a gingival-region diameter of 2.56 mm. The screw threads on the shaft may have a truncated-peak diameter of 2.90 mm.

Figure 1:
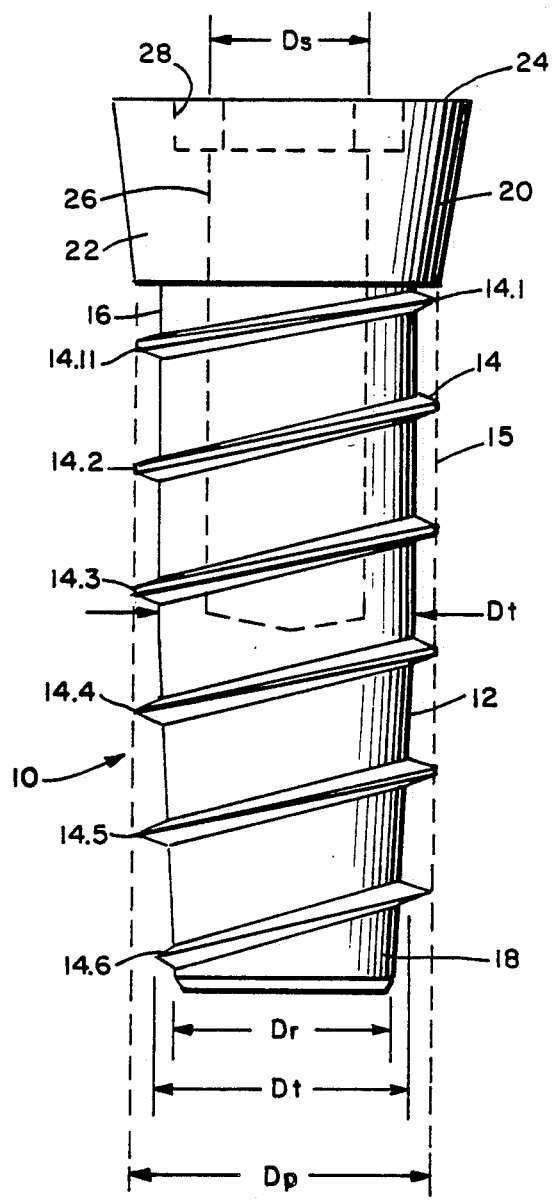
FIG. 1 is a longitudinal side view of a dental implant fixture according to the invention.
Figure 3:
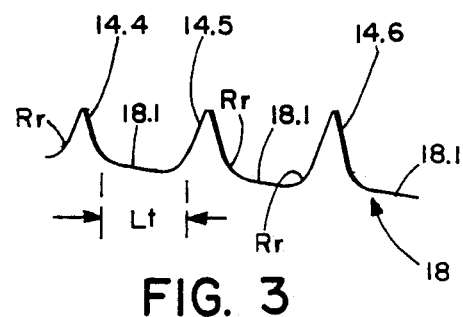
Figure 4:
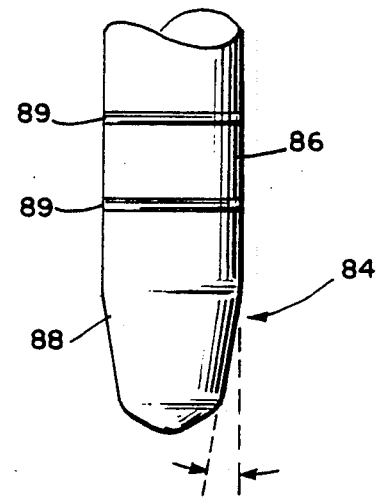
Figure 5:
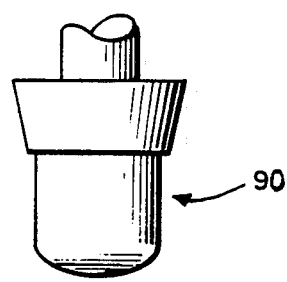

FIG. 3 schematically illustrates a detail of the screw-thread configuration of the fixture of FIG. 1;

FIG. 4 is an outline view of a bone drill for preparing a female bore to accept an implant fixture of the invention; and FIG. 5 is an outline view of a counter-sink useful to prepare a bore to accept such a fixture.

Figure 2:
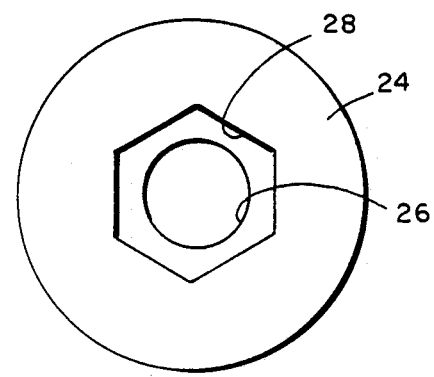
FIG. 2 is an end view of the gingival aspect of the implant fixture illustrated in FIG. 1.

Referring now to FIGS. 1 and 2, the dental implant fixture 10 has a partially-tapered main body shaft 12 bearing screwthreads 14 having peaks truncated on a cylindrical locus 15 of diameter Dp. The roots of the screw threads lie on the surface of the shaft 12. The gingival region 16 of the shaft has a diameter Dt that is less than the diameter Dp of the threadpeak cylinder locus 15. At the apical end 18 the shaft is tapered down to a smaller diameter Dr. The threads 14 are accordingly deeper at the apical end 18 than at the gingival end 16 of the shaft 12. A smooth-sided cap 20 at the gingival end of the shaft completes the fixture. The sides 22 of this cap are smooth and taper outwardly toward the gingival surface 24 of the fixture 10. A receiving bore 26 of diameter Ds, proceeding axially into the fixture from the gingival surface is provided for receiving a transitional component for supporting a prosthodontic restoration (not shown).

A non-circular, here hexagonal-shaped, female socket 28 in the gingival surface 24 surrounds the opening into the receiving bore, for providing anti-rotation to such a component. The choice of a female socket 28 contributes to successfully making a small-diameter implant fixture. The diameter of the shaft 12 at the bottom of the bore 26 is marked Dt.

The tapered shape can be applied to the shaft 12 gradually from its gingival end to its apical end. Preferably, the shaft should be partly cylindrical and partly tapered, as is explained above with reference to in the embodiment illustrated in FIG. 1. The implant fixture 10 has a single-lead thread 14 coiled around the shaft 12 with substantial shaft surface exposed between successive turns 14.1–14.6 of the thread. The spacing between successive turns of the thread 14 may be approximately the same as, or greater than, the thread-root thickness. In the preferred embodiment illustrated, the shaft is cylindrical from its gingival end 16 to the bottom of the bore 26, that is, from turn 14.1 to turn 14.3, following which the shaft tapers to a smaller diameter toward its apical end 18. Three turns 14.4 to 14.6 are borne on the tapered portion of the shaft. In general, the fixture 10 is conical at the apical end 18; and blends into a cylindrical section in the vicinity of the internal bore 26. The purpose of this contour is to preserve a substantially uniform minimum wall thickness of the fixture around the bore 26, while maintaining full thread depth at the apical end. The thread 14.1 nearest the cap 20 has a land 14.11 where its peak is truncated on the locus of the cylinder 15. The two succeeding threads have a similar land. The land gradually diminishes in width from thread 14.4 to thread 14.6, where the land is narrowest, and may disappear entirely.

FIG. 3 is an expanded view showing the contours of the final three turns 14.4, 14.5 and 14.6 and the tapering shaft surface portion 18.1 beside and between successive pairs of them. On the tapering surface 18.1 the threads are deeper than the threads on the cylindrical portion of the shaft toward its gingival end 16. The roots of the threads curve gradually into the sidewall of the shaft 18.1 on a radius Rr; this root feature is used along the entire length of the shaft. There are preferably no sharp-angled meeting surfaces, so that stress concentrations are reduced, which minimizes the chances of breaking the ultra-slim implant fixture.

While use of the invention has been illustrated in connection with currently-available implant systems, it will be understood that the invention can be practiced with any other system now or future existing.

To achieve the objects of the invention careful attention was given to dimensions and materials chosen. Dimensionally, the design is based on the need to:

1. use as large an abutment screw (not shown) as possible; (e.g.: a screw having a minimum diameter of 1.8 mm at the thread peaks); and 2. restrict the implant thread-peak diameter to 2.9 mm or smaller. Typical dimensions of the fixture shown in FIG. 1 are: Ds=1.8 mm; Dp=2.80 mm; Dr=2.21 mm; and Dt=2.56 mm. In FIG. 3, Lt=0.36 mm; and Rr=0.05 mm. However, as is mentioned above, Lt may be larger than the thread-root thickness. Owing to the ultra-small diameter of the new fixture, pure titanium was deemed inadequately strong; a stronger alloy is preferred. A suitable alloy is "TiA16-4V".

Taking into consideration the convenience of oral surgeons and periodontists, to whom the invention is addressed, the new implant fixture is preferably self-tapping, and its shape does not require a special surgical drill for each implant length. Implant fixtures according to the invention can be provided in a variety of lengths, e.g.: 8, 10, 13 and 15 mm. A bone drill 84 contoured as shown in FIG. 4 can be used for all such lengths. The main drill shaft 86 is of uniform diameter and the apical end 88 is tapered, conforming in this illustration to the shape of the shaft 12 of the implant fixture 10 shown in FIG. 1. Depth bands 89 are marked on the main shaft 86, one for each depth of prepared bore intended to be drilled. A counter-sink 90 shown in outline in FIG. 5 can provide a tapered opening into the prepare bore in the jawbone (not shown) conforming (for example) to the shape of the gingival cap 20, so that the side walls of the implant fixture will everywhere be in contact with the host bone.

When a suitable prepared bore is drilled in the host jawbone, the shaft of the implant fixture will fit snugly into it, and the threads of the fixture will tap into the adjacent bone. Near the apical end of the shaft the threads are deeper and will cut more deeply into the side walls of the prepared bore; near the bottom of the prepared bore the diameter is smaller, owing to the tapered apical end 88 of the drill. This combination of deeper threads at the apical end of the fixture and more bone for them to cut into near the bottom of the prepared bore provides increased thread engagement between the fixture and the bone deep within the bore, and a strong anchor to hold the fixture immobile during the healing process. Elsewhere the threads help to anchor the fixture against axial movement in the prepared bore, while intimate contact between the fixture and the host bone provides the best-known environment for osseointegration to proceed. To this end, the side-walls of the gingival cap 20 are highly polished; in addition, the matching taper provided between the cap and the prepared bore, by use of the countersink 90, provides enhanced environment for successful osseointegration when the cap is pulled tightly into the prepared bore by the deeper threads.

What is claimed is:

1. A dental implant fixture comprising a cylindrical shaft having a gingival end and an apical end, said shaft being externally threaded for engagement in a prepared bore in a patient's jawbone, the threads on said shaft being restricted at their peaks to a cylindrical locus having a substantially constant diameter not exceeding 3.0 mm. from said gingival end to said apical end, an axially-located cylindrical receiving bore opening into said shaft from said gingival end and terminating within said shaft at a location between said ends, the diameter of said shaft around said receiving bore from said gingival end to said location being smaller than 3.0 mm. but not less than about 2.56 mm. and the internal diameter of said receiving bore being not less than about 1.8 mm., said shaft being substantially cylindrial from said gingival end to said location, said shaft tapering to a smaller diameter than said 2.56 mm. from said location to said apical end.

2. A dental implant fixture according to claim 1 having anti-rotation means in said gingival region surrounding the opening into said receiving bore, for engaging prosthodontic support means with means to prevent rotation between such support means and said shaft around said tubular axis.

3. A dental implant fixture according to claim 2 in which said anti-rotation means is a non-circular female socket in the gingival aspect surface of said gingival region.

4. A dental implant fixture according to claim 1 in which the diameter of said shaft at the roots of said screw threads is in the range from about 2.2 mm at said apical end to about 2.5 mm toward said location.

5. A dental implant fixture according to claim 1 in which said screw threads consists essentially of a single thread coiled around said shaft with adjacent turns spaced axially apart on said shaft a distance which is at least approximately as great as the root thickness of said threads.

6. A dental implant fixture according to claim 5 in which said distance is about 0.36 mm.

7. A dental implant fixture according to claim 1 in which said gingival region includes a head cap which has a smooth side surface devoid of said thread means.

8. A dental implant fixture according to claim 7 in which said cap expands in diameter from said shaft to a gingival-aspect surface which normally lies substantially flush with said gingival aspect of said jawbone when said fixture is installed in said bore.

* * * * *